US010561682B1

(12) United States Patent
Boston

(10) Patent No.: US 10,561,682 B1
(45) Date of Patent: Feb. 18, 2020

(54) TREATMENT OF ISCHEMIC CONDITIONS, HYPOXIC CONDITIONS, CONDITIONS RELATED TO A HYPOXIA-INDUCTION FACTOR, OR CONDITIONS RELATED TO REACTIVE OXYGEN SPECIES WITH OXYGEN-CONTAINING LIQUIDS

(71) Applicant: Judith Boston, Manhattan Beach, CA (US)

(72) Inventor: Judith Boston, Manhattan Beach, CA (US)

( * ) Notice: Subject to any disclaimer, the term of this patent is extended or adjusted under 35 U.S.C. 154(b) by 0 days.

(21) Appl. No.: 16/371,398

(22) Filed: Apr. 1, 2019

(51) Int. Cl.
*A61K 33/40* (2006.01)
*A61K 9/00* (2006.01)
*A61P 27/02* (2006.01)
*A61P 9/10* (2006.01)
*A61K 31/327* (2006.01)

(52) U.S. Cl.
CPC ............ *A61K 33/40* (2013.01); *A61K 9/0048* (2013.01); *A61K 9/0053* (2013.01); *A61P 9/10* (2018.01); *A61P 27/02* (2018.01); *A61K 31/327* (2013.01)

(58) Field of Classification Search
None
See application file for complete search history.

(56) References Cited

U.S. PATENT DOCUMENTS

| | | | | |
|---|---|---|---|---|
| 5,569,180 A | * | 10/1996 | Spears | A23L 2/54 128/898 |
| 5,770,628 A | * | 6/1998 | Cantoro | A61K 9/0048 514/778 |
| 5,792,090 A | * | 8/1998 | Ladin | A61L 15/18 424/449 |
| 8,802,049 B2 | | 8/2014 | Farone et al. | |
| 2002/0164379 A1 | * | 11/2002 | Nishihara | A61K 9/0048 424/600 |
| 2003/0232114 A1 | * | 12/2003 | Dekleva | A23L 2/54 426/312 |
| 2007/0128241 A1 | * | 6/2007 | Boston | A61K 9/08 424/423 |
| 2008/0146679 A1 | * | 6/2008 | Archambeau | A61K 9/0048 351/159.68 |
| 2010/0151041 A1 | * | 6/2010 | Eckert | A61K 33/00 424/600 |
| 2018/0093995 A1 | | 4/2018 | Gustafson et al. | |

FOREIGN PATENT DOCUMENTS

WO 2016164412 A1 10/2016

OTHER PUBLICATIONS

Tezel, G. et al., Hypoxia-Inducible Factor 1a in the Glaucomatous Retina and Optic Nerve Head, Archives of Ophthalmology, Sep. 2004, 122(9), 1348-1356.

Grimm, C. et al, Hypoxia in the Eye: A Two-Sided Coin, High Altitude Medicine & Biology, Sep. 2012, 13(3), 169-175.

\* cited by examiner

*Primary Examiner* — Jeffrey S Lundgren
*Assistant Examiner* — Michael J Schmitt
(74) *Attorney, Agent, or Firm* — Maschoff Brennan; Brent A. Johnson

(57) ABSTRACT

This disclosure relates to the use of an oxygen-containing liquid for treating conditions related to ischemia, hypoxia, an alteration in electrochemistry, VEGF, HIF, or a reactive oxygen species, and other conditions.

15 Claims, 1 Drawing Sheet

TREATMENT OF ISCHEMIC CONDITIONS, HYPOXIC CONDITIONS, CONDITIONS RELATED TO A HYPOXIA-INDUCTION FACTOR, OR CONDITIONS RELATED TO REACTIVE OXYGEN SPECIES WITH OXYGEN-CONTAINING LIQUIDS

BACKGROUND

There is a continuing need for effective methods of treating ischemic conditions and other conditions related to hypoxia.

SUMMARY

This disclosure relates to the use of an oxygen-containing liquid for treating conditions related to ischemia, hypoxia, an alteration in electrochemistry, VEGF, HIF, or a reactive oxygen species, and other conditions.

Some embodiments include a method of treating an ocular condition comprising administering or delivering an oxygen-containing liquid to the eye of a mammal suffering from an ocular condition.

DETAILED DESCRIPTION

Figure 1:
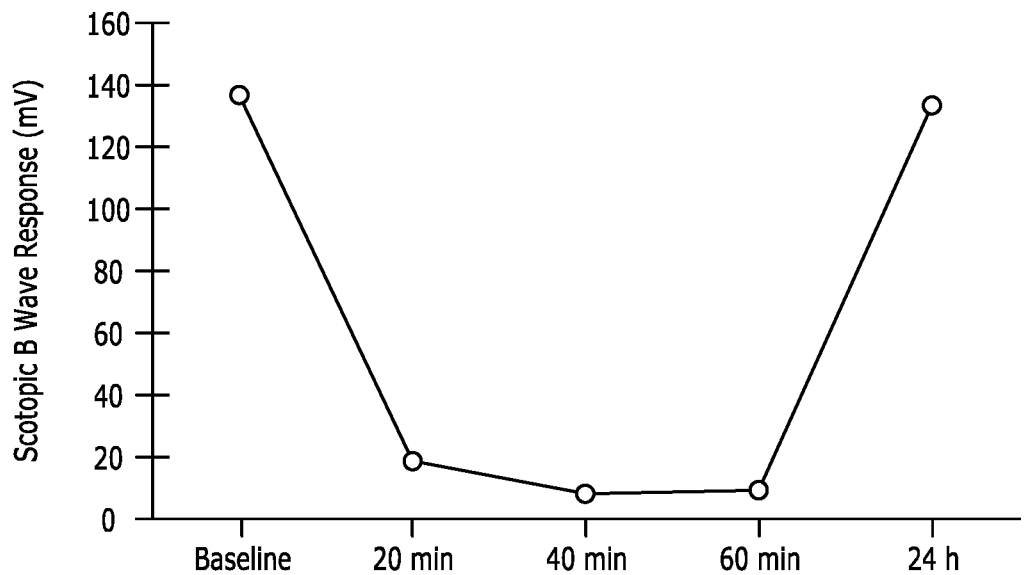
FIG. 1 depicts the scotopic b-wave response of ischemic rabbit eyes subjected to treatment with a hyperbaric oxygen solution as compared to controls.

This disclosure relates to methods of treating ischemic conditions, such as ocular ischemic conditions, other conditions related to hypoxia, or conditions related to reactive oxygen species, comprising administering or delivering an oxygen-containing liquid to a mammal, such as a human being, for the treatment of the condition.

The term "treating" or "treatment" broadly includes any kind of treatment activity, including the diagnosis, cure, mitigation, or prevention of disease in man or other animals, or any activity that otherwise affects the structure or any function of the body of man or other animals.

The oxygen-containing liquid may be any liquid composition containing oxygen, or a compound that provides an oxygen pressure to a liquid, which is suitable for use in a mammal, including a human being, for therapeutic purposes. The oxygen-containing liquid may be aqueous, or may be based upon a suitable organic solvent, or may be a combination of aqueous and organic solvents. The liquid may be in the form of a solution, or a multiple phase liquid, such as a suspension, a colloid, an emulsion, a shear-thinning gel, etc. For many routes of administration, such as injections, it may be important for the oxygen-containing liquid to be sterile.

In some embodiments, rather than being directly administered, an oxygen-containing liquid may be generated in the target tissue by inserting an implant into or near the target tissue. For example, the implant could comprise a biodegradable or bioerodible polymer having components of an oxygenating composition dispersed in the polymer. As the polymer degrades or erodes, the components of the oxygenating composition will mix in the aqueous environment of the tissue into which the implant is inserted, thus generating an oxygen-containing liquid at or near the tissue to be targeted.

The oxygen-containing liquid may have a higher partial oxygen pressure than plain water, for example, the oxygen-containing liquid may have an oxygen pressure that is at least 120 mmHg, at least 140 mmHg, at least 145 mmHg, at least 150 mmHg, at least 155 mmHg, at least 160 mmHg, at least 165 mmHg, at least 170 mmHg, up to 180 mmHg, up to 200 mmHg, up to about 250 mmHg, up to about 300 mmHg, up to about 350 mmHg, up to about 400 mmHg, up to about 450 mmHg, up to about 500 mmHg, about 120-500 mmHg, about 20-40 mmHg, about 40-60 mmHg, about 60-80 mmHg, about 80-100 mmHg, about 100-120 mmHg, about 120-140 mmHg, about 140-145 mmHg, about 145-150 mmHg, about 150-155 mmHg, about 155-160 mmHg, about 160-165 mmHg, about 165-170 mmHg, about 170-175 mmHg, about 175-180 mmHg, about 140-150 mmHg, about 150-160 mmHg, about 160-170 mmHg, about 170-180 mmHg, about 180-190 mmHg, about 190-200 mmHg, about 200-210 mmHg, about 210-220 mmHg, about 220-230 mmHg, about 230-240 mmHg, about 240-250 mmHg, about 250-260 mmHg, about 260-270 mmHg, about 270-280 mmHg, about 280-290 mmHg, about 290-300 mmHg, about 300-320 mmHg, about 320-340 mmHg, about 340-360 mmHg, about 360-380 mmHg, about 380-400 mmHg, about 400-420 mmHg, about 420-440 mmHg, about 440-460 mmHg, about 460-480 mmHg, about 480-500 mmHg, about 140-160 mmHg, about 160-180 mmHg, about 180-200 mmHg, about 160-200 mmHg, about 200-250 mmHg, about 250-300 mmHg, about 300-350 mmHg, about 350-400 mmHg, about 400-450 mmHg, about 450-500 mmHg, about 140-200 mmHg, about 200-300 mmHg, about 300-400 mmHg, about 400-500 mmHg, 500-750 mmHg, 750-1,000 mmHg, 1,000-1,250 mmHg, 1,250-1,500 mmHg, about 175 mmHg, or any oxygen pressure in a range bounded by any of these values. In some embodiments, the oxygen-containing liquid is a hyperbaric oxygen solution (e.g. Examples 1-3 below).

While there may be many ways to add oxygen to a liquid, some oxygen-containing liquids may containing an oxygenating composition, such as a compound, or a combination of compounds, that release an oxygen gas. Suitable oxygenating compositions may contain metal oxides (such as CaO, MgO, etc.), metal hydroxides (such as $Ca(OH)_2$, $Mg(OH)_2$), peroxides (such as hydrogen peroxide or an organic peroxide), or combinations thereof. Other ingredients may be added to increase or reduce the rate of oxygen release, depending upon the particular need. For example, faster oxygen release may provide higher oxygen pressure. On the other hand, slower oxygen release may provide a longer, more consistent, or more sustained, oxygen pressure. Examples of suitable oxygenating compositions are described in U.S. Pat. No. 8,802,049, which is incorporated by reference herein in its entirety. One useful oxygenating composition contains about 20-30% $Ca(OH)_2$, about 10-15% $H_2O_2$, about 0.5-5% sodium acetate, about 0.5-5% $KH_2PO_4$, and about 1-20% Carrageenan, based upon the total weight of the oxygen-containing liquid. In some embodiments, the total amount of oxygen atoms present in all metal oxides, metal hydroxides, and peroxides present in the oxygen-containing liquid is about 20-70%, about 20-50%, about 50-70%, about 20-30%, about 30-40%, about 40-50%, about 50-60%, about 60-70%, about 70-90%, or about 80-95% of the total weight of the oxygen-containing liquid.

As mentioned above, the components of these oxygenating compositions, such as metal oxides, metal hydroxides, and/or peroxides, may be dispersed in a bioerodible or biodegradable polymer, such as a silicon-based polymer, a polyester, a polyorthoester, a polyphosphoester, a polycarbonate, a polyanhydride, a polyphosphazene, a polyoxalate, a poly(amino acid), a polyhydroxyalkanoate, a polyethyleneglycol, a polyvinylacetate, a polyhydroxyacid, a polyanhydride, or copolymer or blend thereof (e.g. a co-polymer of lactic and glycolic acid).

An oxygen-containing liquid may be formulated for any desirable route of delivery including, but not limited to, parenteral, intravenous, intradermal, subcutaneous, oral, inhalative, transdermal, topical to an eye or to skin, transmucosal, rectal, intravaginal, intraperitoneal, buccal, and intraocular.

Appropriate excipients for use in an oxygen-containing liquid may include, for example, one or more carriers, binders, fillers, vehicles, tonicity agents, buffers, disintegrants, surfactants, dispersion or suspension aids, thickening or emulsifying agents, preservatives, lubricants and the like or combinations thereof, as suited to a particular dosage from desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. This document is incorporated herein by reference in its entirety.

In addition to solvent, oxygen, and/or oxygenating compositions, a liquid dosage form for IV, injection (e.g. intraocular injection), topical (e.g. to an eye), or oral administration to a mammal, including a human being, may contain excipients such as bulking agents (such as mannitol, lactose, sucrose, trehalose, sorbitol, glucose, raffinose, glycine, histidine, polyvinylpyrrolidone, etc.), tonicity agents (e.g. dextrose, glycerin, mannitol, sodium chloride, etc.), buffers (e.g. acetate, e.g. sodium acetate, acetic acid, ammonium acetate, ammonium sulfate, ammonium hydroxide, citrate, tartrate, phosphate, triethanolamine, arginine, aspartate, benzenesulfonic acid, benzoate, bicarbonate, borate, carbonate, succinate, sulfate, tartrate, tromethamine, diethanolamine etc.), preservatives (e.g. phenol, m-cresol, a paraben, such as methylparaben, propylparaben, butylparaben, myristyl gamma-picolinium chloride, benzalkonium chloride, benzethonium chloride, benzyl alcohol, 2-penoxyethanol, chlorobutanol, thimerosal, phenymercuric salts, etc.), surfactants (e.g. polyoxyethylene sorbitan monooleate or Tween 80, sorbitan monooleate polyoxyethylene sorbitan monolaurate or Tween 20, lecithin, a polyoxyethylene-polyoxypropylen copolymer, etc.), solvents (e.g. propylene glycol, glycerin, ethanol, polyethylene glycol, sorbitol, dimethylacetamide, Cremophor EL, benzyl benzoate, castor oil, cottonseed oil, N-methyl-2-pyrrolidone, PEG, PEG 300, PEG 400, PEG 600, PEG 600, PEG 3350, PEG 400, poppyseed oil, propylene glycol, safflower oil, vegetable oil, etc.) chelating agents (such as calcium disodium EDTA, disodium EDTA, sodium EDTA, calcium versetamide Na, calteridol, DTPA), or other excipients.

A liquid dosage form comprising an oxygen-containing liquid, e.g. for IV, injection (e.g. intraocular injection), topical (e.g. to an eye), or oral administration, to a mammal, including a human being, may have any suitable pH, such as about 2-12, about 2-4, about 4-6, about 6-8, about 8-10, about 10-12, about 6-7, about 7-8, about 8-9, about 6-6.5, about 6.5-7, about 7-7.5, about 7.5-8, about 8-8.5, about 8.5-9, about 7-7.2, about 7.2-7.4, about 7.4-7.6, about 7.6-7.8, about 7.8-8, or any pH in a range bounded by any of these values.

For many routes of administration, it may be helpful for the oxygen-containing liquid to be hypertonic or hyperosmolar, e.g. having a tonicity or an osmolarity greater than about 290 mOsm/L, such as about 290-600 mOsm/L, about 290-400 mOsm/L, about 400-500 mOsm/L, or about 500-600 mOsm/L; isotonic or isoosmolar, e.g. having a tonicity or an osmolarity near that of the body tissue to which it administered, such as about 290 mOsm/L, about 250-350 mOsm/L, about 250-320 mOsm/L, about 270-310 mOsm/L, or about 280-300 mOsm/L; or hypotonic or hypoosmolar, e.g. having tonicity or an osmolarity less than about 290 mOsm/L, such as about 150-290 mOsm/L, about 150-200 mOsm/L, about 200-290 mOsm/L, about 200-250 mOsm/L, or about 250-290 mOsm/L.

In addition to the above, it may be desirable for an orally administered liquid to contain a sweetening agent such as sucrose or saccharin; or a flavoring agent such as peppermint, methyl salicylate, or orange flavoring.

For creams, gels, ointments, etc. it may be desirable to include thickening agents, such as polyethylene glycol, polyacrylic acid, cetyl alcohol, stearyl alcohol, carnauba wax, stearic acid, hydroxyethylcellulose, guar gum, locust bean gum, xanthan gum, gelatin, silica, bentonite, magnesium aluminum stearate, etc.

Hypoxia, ischemia and reactive metabolites contributes to development and exacerbation of many disease states. The common denominator resulting in inhibition of tissue repair is tissue hypoxia.

Facilitating delivery of oxygen to tissues can result in adjunct and direct treatments in a wide variety of medical conditions.

Tissue hypoxia is low tissue oxygen level, usually related to impaired circulation. Tissue hypoxia, ischemia and reactive metabolites contribute to development and exacerbation of many disease states.

In some embodiments, administering or delivering an oxygen-containing liquid, such as a hyperbaric oxygen-containing liquid, to a mammal suffering from a condition related to ischemia, hypoxia, an alteration in electrochemistry, VEGF, HIF, or a reactive oxygen species, such as an ocular condition related to ischemia, hypoxia, an alteration in electrochemistry, VEGF, HIF, or a reactive oxygen species, results in the Hypoxic Induction Factor (HIF) level of the tissue (e.g. eye tissue) having ischemia to be decreased by at least about 10%, at least about 20%, at least about 30%, at least about 40%, at least about 50%, at least about 60%, at least about 70%, at least about 80%, at least about 90%, or more as compared to the HIF level of the tissue (e.g. eye tissue) having ischemia immediately prior to administration of the oxygen-containing liquid.

In some embodiments, administering or delivering an oxygen-containing liquid, such as a hyperbaric oxygen-containing liquid, to a mammal suffering from a condition related to ischemia, hypoxia, an alteration in electrochemistry, VEGF, HIF, or a reactive oxygen species, such as an ocular condition related to ischemia, hypoxia, an alteration in electrochemistry, VEGF, HIF, or a reactive oxygen species, results in the HIF level of the tissue (e.g. eye tissue) having ischemia to be decreased so that it is within about 50%, within about 40%, within about 30%, within about 20%, within about 10%, within about 5%, within about 3%, or within about 1% of the HIF level of non-ischemic tissue (e.g. the contralateral eye).

In some embodiments, the reduction of the HIF level of the tissue may be observed within 1 day, within 2 days, within 3 days, within 4 days, within 5 days, within 6 days, within 7 days, within 14 days, within 21 days, or within 28 days.

In some embodiments, the reduction of the HIF level of the tissue may be continue for at least 1 day, at least 2 days, at least 3 days, at least 4 days, at least 5 days, at least 6 days, at least 7 days, at least 14 days, at least 21 days, or at least 28 days.

Administering or delivering an oxygen-containing liquid, such as a hyperbaric oxygen-containing liquid, to a mammal may be used to treat any type of ischemic condition, such as wounds, vasculopathies, malignant tumors, arthritis, atherosclerotic plaques, cancers, tumors, burns, inflammatory conditions, including inflammation of neural tissue (e.g. concussion).

In some embodiments, the ischemic condition is an ocular condition, such as diabetic retinopathy, macular degeneration, diabetic macular edema, glaucoma, sickle eye disease, ocular inflammation, hypertensive retinopathy, ocular ischemic syndrome, branched retinal vein occlusion, branched retinal artery occlusion, central retinal vein occlusion, central retinal artery occlusion, retinal detachment, penetrating globe injury, traumatic optic neuropathy, optic neuritis, an inflammatory ocular condition, etc. In some embodiments, the ocular ischemic condition is diabetic retinopathy.

In some embodiments, the ocular ischemic condition is macular degeneration. In some embodiments, the ocular ischemic condition is diabetic macular edema. In some embodiments, the ocular ischemic condition is glaucoma. In some embodiments, the ocular ischemic condition is sickle cell eye disease. In some embodiments, the ocular ischemic condition is an ocular inflammation. In some embodiments, the condition is hypertensive retinopathy. In some embodiments, the condition is ocular ischemic syndrome. In some embodiments, the condition is branched retinal vein occlusion. In some embodiments, the condition is branched retinal artery occlusion. In some embodiments, the condition is central retinal vein occlusion. In some embodiments, the condition is central retinal artery occlusion. In some embodiments, the condition is retinal detachment. In some embodiments, the condition is penetrating globe injury. In some embodiments, the condition is traumatic optic neuropathy. In some embodiments, the condition is optic neuritis. In some embodiments, the condition is an inflammatory ocular condition.

In some embodiments, the ischemic condition is one wherein the electrochemistry is altered, such as heart attack, stroke, neural ischemia, injury to the central nervous system, traumatic brain injury, spinal injury, acute and chronic traumatic encephalopathy, immunocytotoxicity. Administering or delivering an oxygen-containing liquid, such as a hyperbaric oxygen-containing liquid, may also be useful to treat diseases or conditions related to, or caused by, sun damage or oxidation.

Other conditions that may be treated include anemia, migraine headaches, refectory osteomyelitis, etc.

Administering or delivering an oxygen-containing liquid, such as a hyperbaric oxygen-containing liquid, to a mammal may also be used to improve blood oxygen level in chronic diseases and to reduce the need for blood transfusions.

Administering or delivering an oxygen-containing liquid, such as a hyperbaric oxygen-containing liquid, to a mammal suffering from a condition related to ischemia, hypoxia, an alteration in electrochemistry, VEGF, HIF, or a reactive oxygen species, such as an ocular condition related to ischemia, hypoxia, an alteration in electrochemistry, VEGF, HIF, or a reactive oxygen species, may result in an increase in ERG function of the ischemic tissue. For example, the scotopic b-wave response of an eye having ischemia may be about 0-5 mV, about 5-10 mV, about 10-15 mV, about 15-20 mV, about 20-50 mV, about 50-100 mV, or about 100-120 mV.

In some embodiments, administering or delivering an oxygen-containing liquid, such as a hyperbaric oxygen-containing liquid, to a mammal suffering from an ocular ischemic condition results in the scotopic b-wave response of the eye having ischemia to be increased by at least about 20 mV, at least about 30 mV, at least about 40 mV, at least about 50 mV, at least about 60 mV, at least about 70 mV, at least about 80 mV, at least about 90 mV, at least about 100 mV, or more, as compared to the scotopic b-wave response of the eye having ischemia immediately prior to administration of the oxygen-containing liquid.

In some embodiments, administering or delivering an oxygen-containing liquid, such as a hyperbaric oxygen-containing liquid, to a mammal suffering from a condition related to ischemia, hypoxia, an alteration in VEGF, HIF, electrochemistry, or a reactive oxygen species, such as an ocular condition related to ischemia, hypoxia, an alteration in VEGF, HIF, electrochemistry, or a reactive oxygen species, results in the scotopic b-wave response of the tissue (e.g. eye tissue) having ischemia to be increased by at least 2-fold, 3-fold, 4-fold, 5-fold, 6-fold, 7-fold, 8-fold, 9-fold, 10-fold, or more as compared to the scotopic b-wave response of the tissue (e.g. eye tissue) having ischemia immediately prior to administration of the oxygen-containing liquid.

In some embodiments, administering or delivering an oxygen-containing liquid, such as a hyperbaric oxygen-containing liquid, to a mammal suffering from a condition related to ischemia, hypoxia, an alteration in VEGF, HIF, electrochemistry, or a reactive oxygen species, such as an ocular condition related to ischemia, hypoxia, an alteration in VEGF, HIF, electrochemistry, or a reactive oxygen species, results in the scotopic b-wave response of the tissue (e.g. eye tissue) having ischemia to be increased so that it is within about 50%, within about 40%, within about 30%, within about 20%, within about 10%, within about 5%, within about 3%, or within about 1% of the scotopic b-wave response of normal or non-ischemic tissue (e.g. the contralateral eye).

In some embodiments, the improvement in ERG function may be observed within 1 day, within 2 days, within 3 days, within 4 days, within 5 days, within 6 days, within 7 days, within 14 days, within 21 days, or within 28 days.

In some embodiments, administering or delivering an oxygen-containing liquid, such as a hyperbaric oxygen-containing liquid, to a mammal suffering from a condition related to ischemia, hypoxia, an alteration in electrochemistry, VEGF, HIF, or a reactive oxygen species, such as an ocular condition related to ischemia, hypoxia, an alteration in electrochemistry, VEGF, HIF, or a reactive oxygen species, results in the Vascular Endothelial Growth Factor (VEGF) level of the tissue (e.g. eye tissue) having ischemia to be decreased by at least about 10%, at least about 20%, at least about 30%, at least about 40%, at least about 50%, at least about 60%, at least about 70%, at least about 80%, at least about 90%, or more as compared to the VEGF level of the tissue (e.g. eye tissue) having ischemia immediately prior to administration of the oxygen-containing liquid.

In some embodiments, administering or delivering an oxygen-containing liquid, such as a hyperbaric oxygen-containing liquid, to a mammal suffering from a condition related to ischemia, hypoxia, an alteration in electrochemistry, VEGF, HIF, or a reactive oxygen species, such as an ocular condition related to ischemia, hypoxia, an alteration in electrochemistry, VEGF, HIF, or a reactive oxygen species, results in the VEGF level of the tissue (e.g. eye tissue) having ischemia to be decreased so that it is within about 50%, within about 40%, within about 30%, within about 20%, within about 10%, within about 5%, within about 3%, or within about 1% of the VEGF level of normal or non-ischemic tissue (e.g. the contralateral eye).

In some embodiments, the reduction in the VEGF level of the tissue may be observed within 1 day, within 2 days, within 3 days, within 4 days, within 5 days, within 6 days, within 7 days, within 14 days, within 21 days, or within 28 days.

The following embodiments are specifically contemplated.

Embodiment 1

A method of treating a mammal suffering from a condition related to ischemia, hypoxia, an alteration in electrochemistry, VEGF, HIF, or a reactive oxygen species, comprising delivering an oxygen-containing liquid to the mammal suffering from the condition, wherein the treatment results in a therapeutic effect on the condition.

Embodiment 2

The method of embodiment 1, wherein the condition is ocular and the oxygen-containing liquid is delivered to the eye of the mammal.

Embodiment 3

The method of embodiment 1 or 2, wherein the oxygen-containing liquid has an oxygen pressure that is higher than 140 mmHg.

Embodiment 4

The method of embodiment 1, 2, or 3, wherein the oxygen-containing liquid contains a compound that releases an oxygen gas.

Embodiment 5

The method of embodiment 1, 2, 3, or 4, wherein the oxygen-containing liquid has an osmolarity of about 250 mOsm/L to about 350 mOsm/L.

Embodiment 6

The method of embodiment 1, 2, 3, 4, or 5, wherein the oxygen-containing liquid comprises a metal oxide.

Embodiment 7

The method of embodiment 1, 2, 3, 4, 5, or 6, wherein the oxygen-containing liquid comprises a metal hydroxide.

Embodiment 8

The method of embodiment 1, 2, 3, 4, 5, 6, or 7, wherein the oxygen-containing liquid comprises a peroxide.

Embodiment 9

The method of embodiment 1, 2, 3, 4, 5, 6, or 8, wherein the oxygen-containing liquid is sterile.

Embodiment 10

The method of embodiment 1, 2, 3, 4, 5, 6, 7, 8, or 9, wherein the treatment results in an improvement of ERG function within 1 week of administering the oxygen-containing liquid to the eye of the mammal.

Embodiment 11

The method of embodiment 1, 2, 3, 4, 5, 6, 7, 8, 9, or 10, wherein the treatment results in a reduction in VEGF expression within 1 week of administering the oxygen-containing liquid to the eye of the mammal.

Embodiment 12

The method of embodiment 1, 2, 3, 4, 5, 6, 7, 8, 9, 10, or 11, wherein the condition is diabetic retinopathy.

Embodiment 13

The method of embodiment 1, 2, 3, 4, 5, 6, 7, 8, 9, 10, or 11, wherein the condition is macular degeneration.

Embodiment 14

The method of embodiment 1, 2, 3, 4, 5, 6, 7, 8, 9, 10, or 11, wherein the condition is diabetic macular edema.

Embodiment 15

The method of embodiment 1, 2, 3, 4, 5, 6, 7, 8, 9, 10, or 11, wherein the condition is sickle cell eye disease.

Embodiment 16

The method of embodiment 1, 2, 3, 4, 5, 6, 7, 8, 9, 10, or 11, wherein the condition is an ocular inflammation.

Embodiment 17

The method of embodiment 1, 2, 3, 4, 5, 6, 7, 8, 9, 10, or 11, wherein the condition is hypertensive retinopathy.

Embodiment 18

The method of embodiment 1, 2, 3, 4, 5, 6, 7, 8, 9, 10, or 11, wherein the condition is ocular ischemic syndrome.

Embodiment 19

The method of embodiment 1, 2, 3, 4, 5, 6, 7, 8, 9, 10, or 11, wherein the condition is branched retinal vein occlusion.

Embodiment 20

The method of embodiment 1, 2, 3, 4, 5, 6, 7, 8, 9, 10, or 11, wherein the condition is branched retinal artery occlusion.

Embodiment 21

The method of embodiment 1, 2, 3, 4, 5, 6, 7, 8, 9, 10, or 11, wherein the condition is central retinal vein occlusion.

Embodiment 22

The method of embodiment 1, 2, 3, 4, 5, 6, 7, 8, 9, 10, or 11, wherein the condition is central retinal artery occlusion.

Embodiment 23

The method of embodiment 1, 2, 3, 4, 5, 6, 7, 8, 9, 10, or 11, wherein the condition is retinal detachment.

Embodiment 24

The method of embodiment 1, 2, 3, 4, 5, 6, 7, 8, 9, 10, or 11, wherein the condition is penetrating globe injury.

Embodiment 25

The method of embodiment 1, 2, 3, 4, 5, 6, 7, 8, 9, 10, or 11, wherein the condition is traumatic optic neuropathy.

Embodiment 26

The method of embodiment 1, 2, 3, 4, 5, 6, 7, 8, 9, 10, or 11, wherein the condition is optic neuritis.

Embodiment 27

The method of embodiment 1, 2, 3, 4, 5, 6, 7, 8, 9, 10, or 11, wherein the condition is an inflammatory ocular condition.

Embodiment 28

The method of embodiment 1, 2, 3, 4, 5, 6, 7, 8, 9, 10, 11, 12, 13, 14, 15, 16, 17, 18, 19, 20, 21, 22, 23, 24, 25, 26, or 27, wherein the oxygen-containing liquid is injected into an eye of a human being.

Embodiment 29

The method of embodiment 1, 2, 3, 4, 5, 6, 7, 8, 9, 10, 11, 12, 13, 14, 15, 16, 17, 18, 19, 20, 21, 22, 23, 24, 25, 26, or 27, wherein the oxygen-containing liquid is topically administered to a human being.

Embodiment 30

The method of embodiment 1, 2, 3, 4, 5, 6, 7, 8, 9, 10, 11, 12, 13, 14, 15, 16, 17, 18, 19, 20, 21, 22, 23, 24, 25, 26, or 27, wherein the oxygen-containing liquid is orally administered to a human being.

Example 1

The effect of a hyperbaric oxygen solution in ischemic rabbit eyes was evaluated. Ischemia was induced in six rabbits as follows. A needle was connected to a saline bag, which was elevated to create pressure at the needle opening. The needle was placed into the rabbit eye and the intraocular pressure was allowed rise in the rabbit eyes for 90 minutes, which caused ischemia in the rabbit eyes. Rabbit 1 received no treatment, but then received an intraocular injection of the hyperbaric oxygen solution an hour after the needle attached to the saline bag was removed. Rabbits 2-3 were intraocularly injected with normal saline (with an oxygen pressure of 112.6 mmHg) 20 minutes after the needle attached to the saline bag was removed. Rabbits 4-6 were intraocularly injected with a hyperbaric oxygen solution (with an oxygen pressure of 175.2 mmHg) 20 minutes after the needle attached to the saline bag was removed. The results are depicted in Table 1 and FIG. 1.

TABLE 1

| | | | Scotopic B Wave Response (mV) | | | |
|---|---|---|---|---|---|---|
| Rabbit | Treatment | Baseline | 20 min after ischemia | 40 min after ischemia | 60 min after ischemia | 24 hr after ischemia |
| 1 | None | 136.9 | 18.52 | 7.8 | 8.85 | 133.4 |
| 2 | Saline | 155.4 | 16.65 | 12.03 | — | |
| 3 | Saline | 192.8 | 33.76 | 15.6 | 12.32 | |
| 4 | Hyperbaric oxygen | 136.1 | 11.46 | 22.17 | 25.8 | |
| 5 | Hyperbaric Oxygen | — | 19.43 | 28.4 | 48.6 | |
| 6 | Hyperbaric Oxygen | — | 50.4 | 75.07 | 94.45 | |

Example 2

ARPE-19 cells were treated with a hyperbaric oxygen solution (oxygen pressure of 175.2 mmHg) and placed into a hypoxic chamber for 48 hours. Control cells were incubated in the hypoxic chamber without the hyperbaric oxygen solution. Phase contrast images show that the hypoxic ARPE-19 cells rounded up and showed unusual morphology compared to the hyperbaric oxygen treated hypoxic cells. There were 71 rounded cells per high power field in the control hypoxic cells versus 8 rounded cells per high power field in the hyperbaric oxygen solution treated hypoxic cells. It was concluded that hyperbaric oxygen solution appears to protect cells from the typical damage that results from exposure to hypoxia.

Example 3

Figure 2:
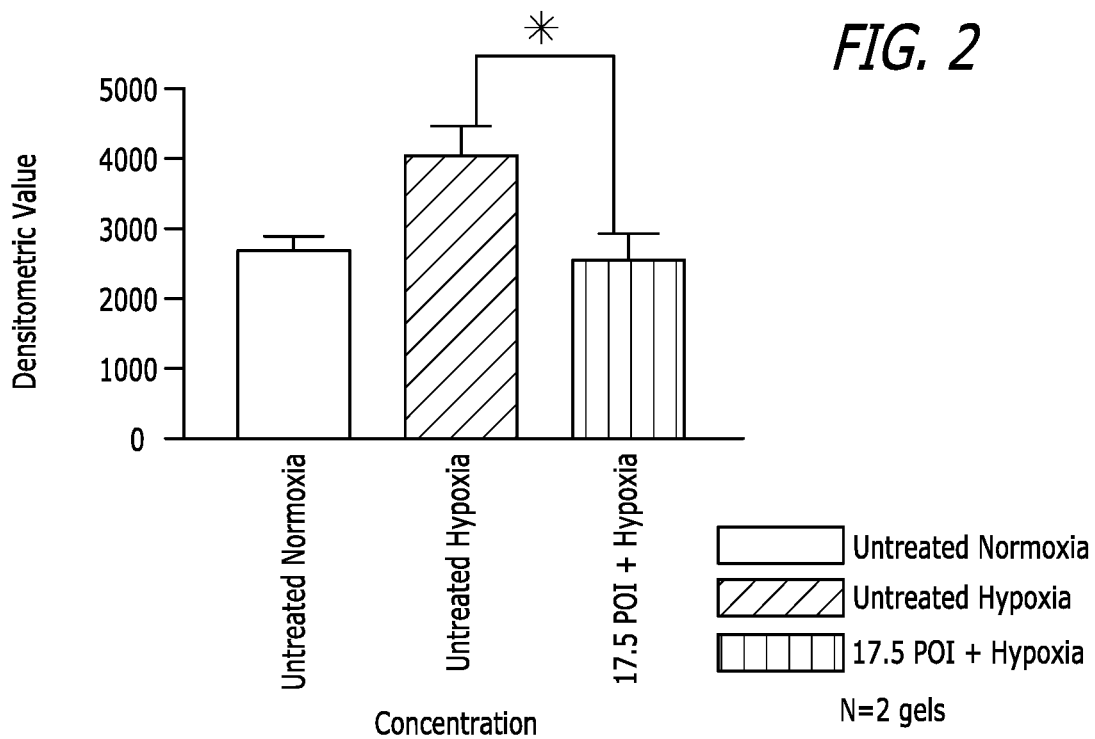
FIG. 2 depicts the levels of VEGF in retinal pigment epithelium (RPE) cells exposed to hypoxic conditions and treated with a hyperbaric oxygen solution.

Retinal pigment epithelium cells were exposed to hypoxic conditions for 48 hours. Treatment with a hyperbaric oxygen solution (oxygen pressure of 175.2 mmHg) resulted in a statistically significant reduction in cellular levels of expressed vascular endothelial growth factor (VEGF) $p<0.05$ (FIG. 2). This indicates that treatment with a hyperbaric oxygen solution normalizes the VEGF level of cells exposed to hypoxic conditions so that they are similar to the basal level of VEGF.

The invention claimed is:

1. A method of treating a condition related to ischemia, hypoxia, a hypoxia-induction factor, or reactive oxygen species comprising injecting a therapeutically effective amount of an oxygen-containing liquid into an eye of a human being suffering from the condition, wherein, when the oxygen-containing liquid is injected into the eye of the human being, the oxygen-containing liquid has an oxygen partial pressure that is higher than 140 mmHg and the oxygen-containing liquid has an oxygen partial pressure that is higher than plain water.

2. The method of claim 1, wherein the oxygen-containing liquid contains a compound that releases an oxygen gas by a chemical reaction.

3. The method of claim 1, wherein the oxygen-containing liquid has an osmolarity of about 250 mOsm/L to about 350 mOsm/L.

4. The method of claim 1, wherein the oxygen-containing liquid comprises a metal oxide.

5. The method of claim 1, wherein the oxygen-containing liquid comprises a metal hydroxide.

6. The method of claim 1, wherein the oxygen-containing liquid comprises a peroxide.

7. The method of claim 1, wherein the oxygen-containing liquid is sterile.

8. The method of claim 1, wherein injecting the oxygen-containing liquid to the human being results in an improvement of ERG function within 1 week of administering the oxygen-containing liquid to the eye of the human being.

9. The method of claim 1, wherein injecting the oxygen-containing liquid to the human being results in a reduction in VEGF expression within 1 week of administering the oxygen-containing liquid to the eye of the human being.

10. The method of claim 1, wherein the condition is diabetic retinopathy.

11. The method of claim 1, wherein the condition is macular degeneration, diabetic macular edema, sickle cell eye disease, an ocular inflammation, hypertensive retinopathy, ocular ischemic syndrome, branched retinal vein occlusion, branched retinal artery occlusion, central retinal vein occlusion, central retinal artery occlusion, or retinal detachment.

12. The method of claim 1, wherein the condition is penetrating globe injury.

13. The method of claim 1, wherein the condition is traumatic optic neuropathy.

14. The method of claim 1, wherein the condition is optic neuritis.

15. The method of claim 1, wherein the condition is an inflammatory ocular condition.

\* \* \* \* \*